United States Patent
Hardin, Jr.

(10) Patent No.: US 9,844,649 B2
(45) Date of Patent: Dec. 19, 2017

(54) TELESCOPIC WIRE GUIDE

(75) Inventor: David M. Hardin, Jr., Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 2286 days.

(21) Appl. No.: 11/825,855

(22) Filed: Jul. 9, 2007

(65) Prior Publication Data

US 2008/0015508 A1 Jan. 17, 2008

Related U.S. Application Data

(60) Provisional application No. 60/819,415, filed on Jul. 7, 2006.

(51) Int. Cl.
| | | |
|---|---|---|
| A61M 25/09 | (2006.01) |
| A61B 1/00 | (2006.01) |
| A61M 25/01 | (2006.01) |
| A61B 1/018 | (2006.01) |
| A61B 1/015 | (2006.01) |

(52) U.S. Cl.
CPC ......... *A61M 25/09* (2013.01); *A61B 1/00087* (2013.01); *A61B 1/015* (2013.01); *A61B 1/018* (2013.01); *A61M 25/0905* (2013.01); *A61M 25/09041* (2013.01); *A61M 2025/0175* (2013.01); *A61M 2025/09116* (2013.01); *A61M 2025/09175* (2013.01)

(58) Field of Classification Search
CPC ... A61B 1/00087; A61B 1/012; A61B 1/0128; A61B 1/273; A61B 1/2733; A61B 1/2736; A61B 1/2676; A61B 1/31; A61M 25/09; A61M 25/09041; A61M 25/0905; A61M 25/09058; A61M 25/09066; A61M 25/09075; A61M 25/09083; A61M 25/09091; A61M 25/09116; A61M 25/09125; A61M 25/09191
USPC ................ 600/104, 114, 153, 101, 106, 107, 600/139–143, 154; 604/158, 164.13, 604/165.01, 165.02, 167.06; 606/205–209
See application file for complete search history.

(56) References Cited

U.S. PATENT DOCUMENTS

| | | | |
|---|---|---|---|
| 4,652,716 A | | 3/1987 | Schneider et al. |
| 5,386,818 A | | 2/1995 | Schneebaum et al. |
| 5,454,822 A | * | 10/1995 | Schob et al. ................ 606/148 |
| 5,506,381 A | | 4/1996 | Matsushima et al. |
| 5,556,551 A | | 9/1996 | Matsushima et al. |
| 5,573,010 A | * | 11/1996 | Pflugbeil ............ A61B 17/3207 600/585 |
| 5,810,876 A | * | 9/1998 | Kelleher ..................... 606/205 |
| 5,820,546 A | | 10/1998 | Ouchi |
| 5,899,850 A | | 5/1999 | Ouchi |
| 5,921,971 A | | 7/1999 | Agro et al. |
| 5,938,586 A | | 8/1999 | Wilk et al. |

(Continued)

*Primary Examiner* — Ryan Henderson
(74) *Attorney, Agent, or Firm* — Brinks Gilson & Lione

(57) ABSTRACT

A telescopic wire guide is disclosed. The telescopic wire guide comprises an outer wire having a proximal end and a distal end. The outer wire has a lumen formed from the proximal end through the distal end. The telescopic wire guide further comprises a core wire disposed within the lumen and slidably movable therealong relative to the outer wire for distally telescopically extending the wire guide a predetermined length.

17 Claims, 3 Drawing Sheets

(56) References Cited

U.S. PATENT DOCUMENTS

| | | | |
|---|---|---|---|
| 6,015,381 A * | 1/2000 | Ouchi | 600/104 |
| 6,132,444 A * | 10/2000 | Shturman et al. | 606/159 |
| 6,428,559 B1 * | 8/2002 | Johnson | 606/200 |
| 6,663,597 B1 * | 12/2003 | Windheuser et al. | 604/165.02 |
| 6,827,683 B2 | 12/2004 | Otawara | |
| 7,384,424 B2 * | 6/2008 | Kusleika et al. | 606/200 |
| 7,628,763 B2 * | 12/2009 | Noriega et al. | 600/585 |
| 2001/0025149 A1 * | 9/2001 | Kobayashi et al. | 600/564 |
| 2001/0044633 A1 * | 11/2001 | Klint | A61B 17/12022 606/200 |
| 2003/0139689 A1 * | 7/2003 | Shturman et al. | 600/585 |
| 2003/0139763 A1 * | 7/2003 | Duerig et al. | 606/198 |
| 2004/0049095 A1 * | 3/2004 | Goto et al. | 600/107 |
| 2004/0116832 A1 * | 6/2004 | Friedrich et al. | 600/585 |
| 2004/0249277 A1 * | 12/2004 | Kato et al. | 600/434 |
| 2005/0004553 A1 * | 1/2005 | Douk | 604/523 |
| 2005/0014995 A1 * | 1/2005 | Amundson et al. | 600/105 |
| 2005/0021075 A1 * | 1/2005 | Bonnette et al. | 606/200 |
| 2005/0043757 A1 * | 2/2005 | Arad | A61B 17/0401 606/200 |
| 2005/0054983 A1 * | 3/2005 | Mullen | 604/164.02 |
| 2005/0148902 A1 * | 7/2005 | Minar et al. | 600/585 |
| 2005/0222583 A1 * | 10/2005 | Cano et al. | 606/108 |
| 2007/0255303 A1 * | 11/2007 | Bakos et al. | 606/185 |
| 2007/0299305 A1 * | 12/2007 | Murakami et al. | 600/106 |
| 2008/0154090 A1 * | 6/2008 | Hashimshony | 600/104 |

* cited by examiner

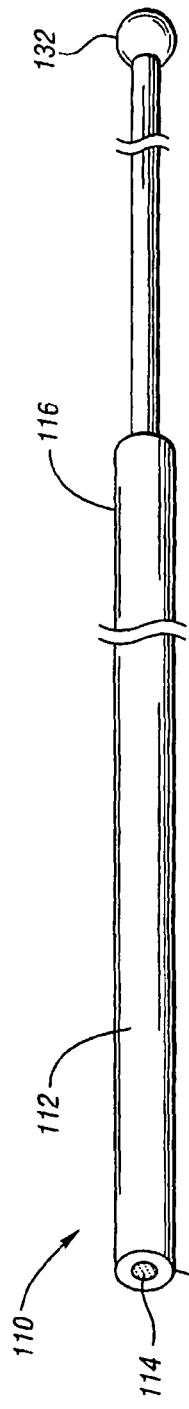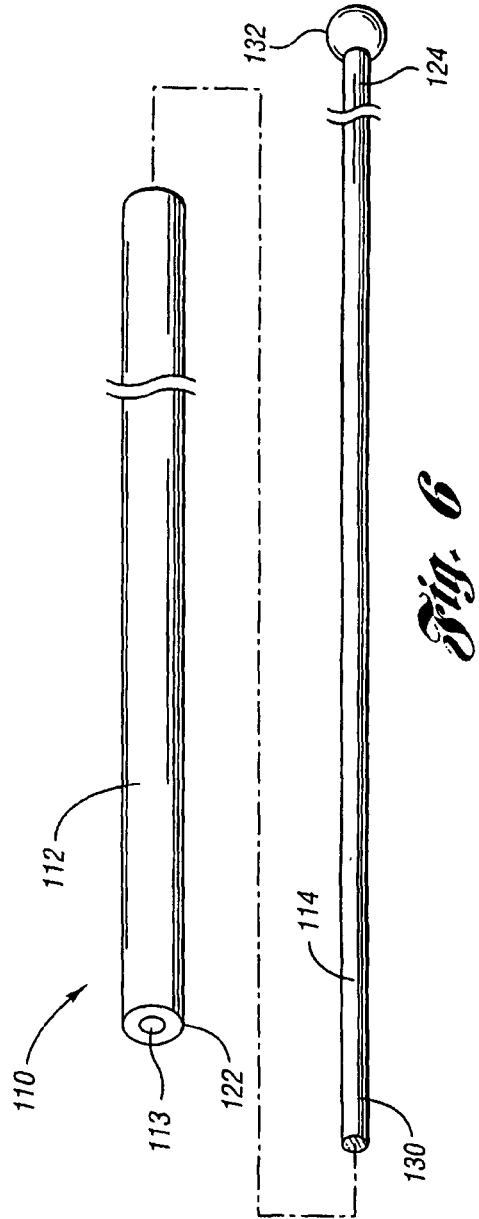

TELESCOPIC WIRE GUIDE

CROSS-REFERENCE TO RELATED APPLICATIONS

This application claims the benefit of U.S. Provisional Application Ser. No. 60/819,415, filed on Jul. 7, 2006, entitled "TELESCOPIC WIRE GUIDE," the entire contents of which are incorporated herein by reference.

BACKGROUND OF THE INVENTION

The present invention relates to telescopic wire guides and apparatus for medical procedures involving endoscopic procedures.

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

The use of endoscopic treatments has recently increased for some diseases occurring in the gastrointestinal or pancreatobiliary duct systems. Endoscope systems are used frequently for diagnostic procedures, including contrast imaging of biliary or pancreatic ducts. Endoscopes are also used in procedures for retrieving gallstones that exist in the common bile duct and elsewhere.

Typically, these treatments are performed in the pancreatic duct, bile duct, and the hepatic duct by positioning the distal end of an endoscope in the vicinity of the duodenal papilla. Once the endoscope is in place, a wire guide is delivered to the target anatomy via the working channel of the endoscope. In order to guide the wire guide (or other medical instruments), out of the working channel of the endoscope. When the distal end of the wire guide is properly oriented, the wire guide is inserted into the target anatomy.

At this point in the procedure, a catheter or similar treatment instrument can be passed over the wire guide either in a conventional over-the-wire style or in a rapid exchange style to the target anatomy. In order to limit movement of the wire guide relative to the target anatomy, the distal or proximal ends of the guide wire can be locked relative to the endoscope.

Traditional gastroenterology accessory techniques require relatively long wires to exchange accessories thereover. Emerging technology in the gastroenterology field uses a relatively short wire guide to perform many exchanges. In many situations, the traditional and new compatible accessories are used during the same procedure, leaving a void in specific wire guide compatibility.

Thus, it is desirable to provide an improved wire guide compatible with traditional and new accessories.

BRIEF SUMMARY OF THE INVENTION

The present invention generally provides a telescopic wire guide that is compatible with traditional and new accessories. Embodiments of the present invention fills the void in specific wire guide compatibility wherein the traditional and new compatible accessories are used during the same procedure.

In one embodiment, the present invention provides a telescopic wire guide. The telescopic wire guide comprises an outer wire having a proximal end and a distal end. The outer wire has a lumen formed from the proximal end through the distal end. The telescopic wire guide further comprises a core wire disposed within the lumen and slidably movable therealong relative to the outer wire for distally telescopically extending the wire guide a predetermined length.

In another embodiment, the telescopic wire guide comprises an outer wire having a proximal end and a distal end. The outer wire has a lumen formed from the proximal end through the distal end. The telescopic wire guide further comprises a core wire disposed within the lumen and slidably movable therealong relative to the outer wire for distally telescopically extending the wire guide a predetermined length. The core wire comprises a proximal portion and a distal portion. The proximal portion comprises a stop to limit distal movement of the core wire, defining the predetermined length that the core wire extends from the outer wire. The core wire has a first length and the outer wire has a second length, the first length being greater than the second length.

In yet another embodiment, the present invention provides an endoscope apparatus having a telescopic wire guide apparatus. The apparatus comprises an endoscopic assembly for endoscopy. The assembly comprises an insertion tube having a plurality of channels through which endoscopic parts may be disposed. The assembly further comprises a control system in mechanical and fluid communication with the insertion tube. The control system is configured to control at least one of the endoscopic parts. The apparatus further comprises a telescopic wire guide disposed in one of the plurality of channels of the endoscopic assembly, the telescopic wire guide comprises an outer wire having a proximal end and a distal end. The outer wire has a lumen formed from the proximal end through the distal end. The wire guide further comprises a core wire disposed within the lumen and slidably movable therealong relative to the outer wire for distally telescopically extending the wire guide a predetermined length.

Further objects, features, and advantages of the present invention will become apparent from consideration of the following description and the appended claims when taken in connection with the accompanying drawings.

BRIEF DESCRIPTION OF THE DRAWINGS

FIG. 4 is side view of the telescopic wire guide in accordance with one embodiment of the present invention;

FIG. 5 is another side view of the telescopic wire guide with a core wire distally extended from an outer wire; and FIG. 6 is an exploded view of the telescopic wire guide in accordance with one embodiment of the present invention.

DETAILED DESCRIPTION OF THE INVENTION

The present invention generally provides a telescopic wire guide and an endoscopic assembly. Embodiments of the present invention provide a wire guide that is convertible to relatively long and short lengths. In one embodiment, the telescopic wire guide includes an outer wire and a core wire disposed within the outer wire and configured to be slideably moveable therealong for additional length of the wire guide.

Figure 1:
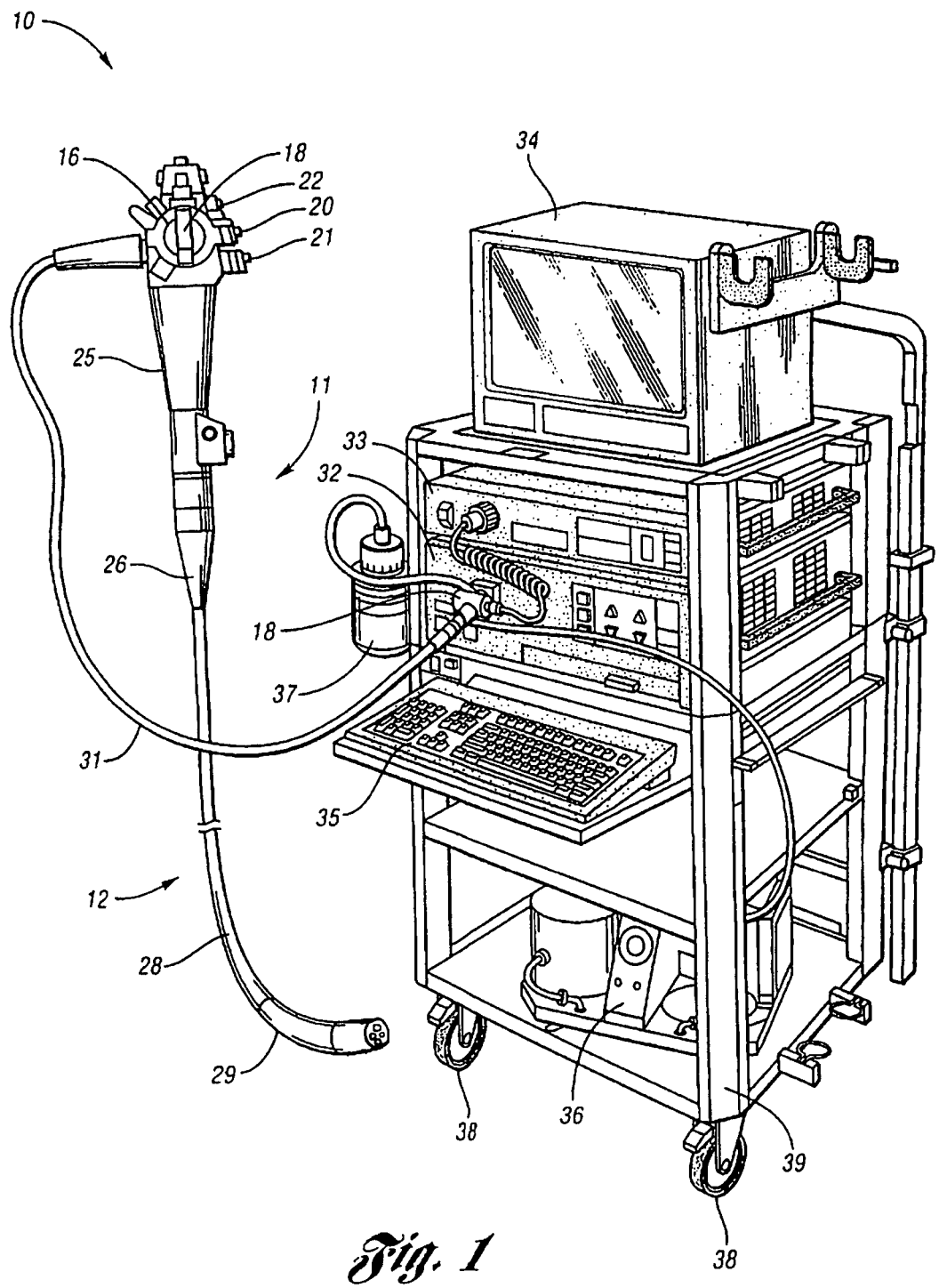
FIG. 1 is a perspective view of an endoscopic system comprising an endoscope having a telescopic wire guide in accordance with one embodiment of the present invention.

FIG. 1 illustrates an endoscopic system 10 comprising an endoscope 11 in accordance with one embodiment of the present invention. In this embodiment, the endoscope 11 comprises an insertion tube 12 to be inserted into a body cavity for various endoscopic procedures including gastroscopy, sigmoidoscopy and colonoscopy, esophago gastro duodenoscopy (EGD), endoscopic retrograde cholangiopancreatography (ERCP), and bronchoscopy. As shown, the endoscope 11 comprises an insertion tube 12 having a plurality of channel ports 13 through which endoscopic units may be disposed. In one embodiment, the endoscopic units disposed in one of the ports may include one embodiment of the telescopic wire guide mentioned above, an endoscopic camera lens 80, a suction source 82, and a water/air flush 84. Other suitable units may be used as desired.

Figure 2:
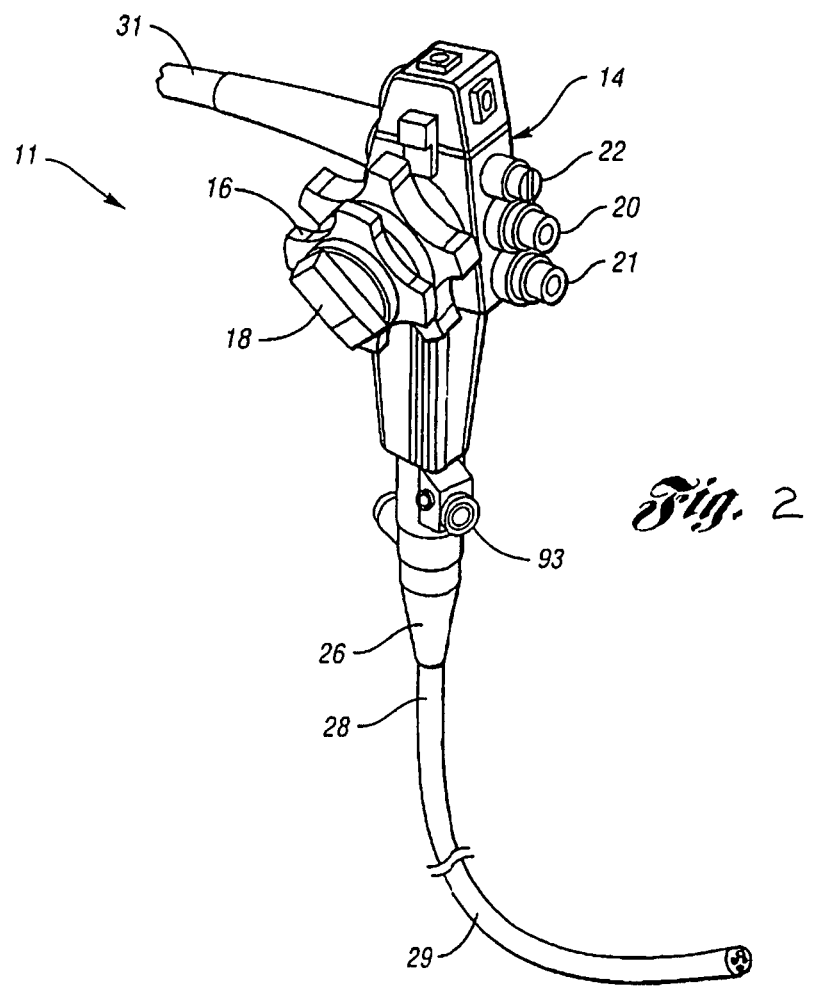
FIG. 2 is a perspective view of the endoscope depicted in FIG. 1.

As shown in FIGS. 1 and 2, the endoscope 11 further includes a control system 14 that is in mechanical and fluid communication with the insertion tube 12. The control system 14 is configured to control the insertion tube 12 and endoscopic parts disposed therein. As shown, the control system 14 includes first and second control knobs 16, 18. The control knobs 16, 18 are configured to be in mechanical communication with the insertion tube 12. The control knobs 16, 18 allow the physician to control and guide, by known means, the insertion tube 12 through vessels and cavities of a patient. The control system 14 further includes valve switches (e.g., suction valve 20, air/water valve 21, camera valve 22), each of which are in communication to one of the channel ports 13 of the insertion tube 12.

For example, the suction valve switch 20, when activated, allows a vacuum from a suction source through a suction channel port for suctioning unwanted plaque and debris from the patient. In one example, the distal end of the insertion tube 12 is inserted, rectally or orally, to a predetermined endoscopic location within a patient. Insertion of the insertion tube 12 may be rectally or orally depending on the endoscopic procedure.

In this embodiment, the insertion tube 12 comprises an operating portion 25 connected to the control system 14 and extending to an insertion portion protecting member 26. A control system 20 is connected to the operating portion 25 and is configured to control the insertion tube 12. In this embodiment, the insertion tube 12 is composed of components that include a flexible tube 28, a flexure 29 connected to the flexible tube 28, and an endoscope tip 30 connect to the flexure 29. A universal cord 31, on one end, is connected and in communication with the control system 20. On the other end, the cord 31 has a connector 18 attached thereto. The connector 18 is in communication to a light guide tube and electrical contact, and is connected to a light source apparatus 32 and an image processing apparatus 33 (external devices). These external devices may include a monitor 34, an input keyboard 35, a suction pump apparatus 36, and an irrigation bottle 37, and other suitable apparatus are installed on a rack 39 equipped with rollers 38.

Figure 3:
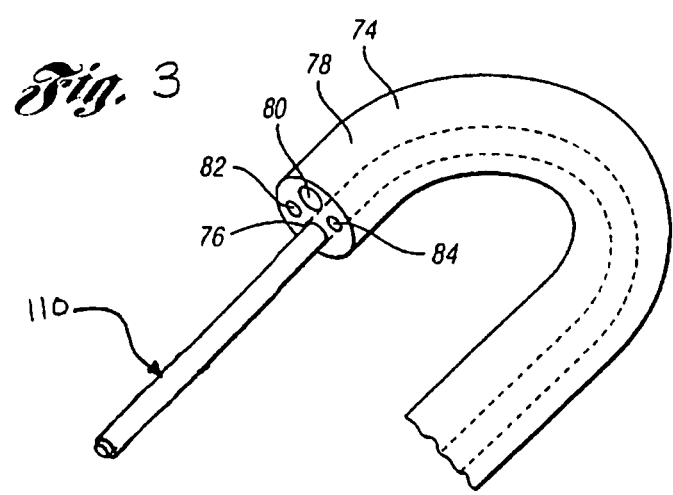
FIG. 3 is an elevated view of a distal tip of the endoscope and the telescopic wire guide in accordance with one embodiment of the present invention.

As shown in FIG. 3, the endoscopic system 10 includes a telescopic wire guide 110 as mentioned above. In this embodiment, the telescopic wire guide 110 is inserted through the channel port 76 of the endoscopic system 10. The telescopic wire guide 110 is then fed through the respective channel port 76 of the endoscopic system 10. The telescopic wire guide is preferably fed therethrough until the distal end 54 of the outer catheter is adjacent nozzle 78 of the insertion tube 12.

FIGS. 4 and 5 illustrate the telescopic wire guide 110 comprising an outer wire 112 and a core wire 114 slidably disposed therethrough. As shown in FIGS. 4-6, the outer wire has a proximal end 116 and a distal end 120. Preferably, the outer wire 112 has a lumen 113 formed from the proximal end 116 through the distal end 120. In this embodiment, the outer wire 112 is a helical coil defining the lumen formed from the proximal end through the distal end thereof. The outer wire 112 may comprise any suitable material. For example, the outer wire 112 may comprise super elastic material, stainless steel wire, nitinol, cobalt-chromium-nickel-molybdenum-iron alloy, or cobalt-chrome alloy. In this embodiment, the outer wire 112 comprises a lubricious outer coat 122 for easy maneuverability with a body vessel.

Preferably, the outer coat comprises elastomeric and polymeric materials, e.g., polytetrafluoroethylene (PTFE), polyethylene, polypropylene, perfluoroelastomer, fluoroelastomer, nitrile, neoprene, polyurethane, silicone, polytetrafluroethylene, styrene-butadiene, rubber, or polyisobutylene. In an alternate embodiment, the outer wire is a nitinol tubing having the lumen formed therethrough.

As shown, the telescopic wire guide further comprises a core wire 114 disposed within the lumen 113 of the outer wire 112. In this embodiment, the core wire 114 is slidably movable along the lumen 113 relative to the outer wire 112 for distally telescopically extending the wire guide 110 to a predetermined length. Preferably, the core wire 114 comprises a proximal portion 124 and a distal portion 130. The proximal portion 124 comprises a stop 132 to limit distal movement of the core wire 110, defining the predetermined length that the core wire 110 extends from the outer wire 112. In this embodiment, the stop 132 has a spherical shape and is integrally formed on the proximal end of the core wire. However, the stop may take on any other suitable shape and may be attached or integrally formed on any proximal portion of the core wire to limit distal movement of the core wire relative to the outer wire.

Preferably, the core wire 110 has a first length and the outer wire has a second length. In this embodiment, the first length being greater than the second length. In this embodiment, the first length may be between about 200 and 300 centimeters (cm), and the second length may be between about 400 and 600 cm. The core wire comprises super elastic material, stainless steel wire, nitinol, cobalt-chromium-nickel-molybdenum-iron alloy, and cobalt-chrome alloy.

In one example, the distal end of the insertion tube 12 is inserted, rectally or orally, to a predetermined endoscopic location within a patient. Insertion of the insertion tube 12 may be rectally or orally depending on the endoscopic procedure. At the location, a physician may activate and control the endoscopic units as desired, such as to cut sutures previously surgically placed in a patient. The endoscope in combination with the telescopic wire guide of the present invention allows the physician to make sharp dissections and cuts as desired.

In use, the telescopic wire guide is cooperable with the endoscopic system 10 mentioned above. The telescopic wire guide 110 may be inserted through the channel port 76 of system 10, wherein both the outer wire guide and the core wire are distally aligned with each other as shown in FIG. 4. When the distal end of the outer wire is at a desirable location, traditional and new accessories may be disposed thereabout as needed. Thereafter, further procedures may be performed at a location further distal from the distal end of the outer wire. This is accomplished by distally moving the core wire relative to the outer wire for additional length. In one embodiment, the length of the outer wire may be between 200 and 300 centimeters (cm), and the length of the core wire may be between about 400 and 600 cm. Thus, the core wire may be advanced distally and additional length to accomplish another procedure thereafter without a need to retract the outer wire and introduce another long wire.

While the present invention has been described in terms of preferred embodiments, it will be understood, of course, that the invention is not limited thereto since modifications may be made to those skilled in the art, particularly in light of the foregoing teachings.

The invention claimed is:

1. A telescopic wire guide configured for insertion through a working channel of an endoscope into a biliary or pancreatic duct, the telescopic wire guide comprising:
   an outer wire having a proximal end and a distal end, the outer wire having a lumen formed from the proximal end through the distal end, the outer wire having a constant outer diameter along its entire length; and
   a core wire disposed within the lumen and slidably movable therealong relative to the outer wire for distally telescopically extending the wire guide a predetermined length, the core wire comprising a proximal portion and a distal portion, the proximal portion comprising a stop to limit distal movement of the core wire, the distal portion defining a distal end that is retractable into the lumen of the outer wire proximally beyond the distal end of the outer wire, wherein the stop abuts the proximal end of the outer wire to define the predetermined length and defining an extended position in which the core wire extends the predetermined length from the outer wire, the core wire having a first length and the outer wire having a second length, the first length being greater than the second length, the core wire configured to slidably retract from the extended position to a retracted position in which the distal portion is disposed entirely within the lumen and the distal end of the core wire is disposed proximally from the distal end of the outer wire;
   wherein the outer wire is a helical coil defining the lumen formed from the proximal end through the distal end thereof.

2. The wire guide of claim 1 wherein the outer wire comprises at least one of super elastic material, stainless steel wire, nitinol, cobalt-chromium-nickel-molybdenum-iron alloy, and cobalt-chrome alloy.

3. The wire guide of claim 2 wherein the outer wire comprises an outer coat.

4. The wire guide of claim 3 wherein the outer coat comprises polytetrafluoroethylene.

5. The wire guide of claim 1 wherein the core wire comprises super elastic material, stainless steel wire, nitinol, cobalt-chromium-nickel-molybdenum-iron alloy, or cobalt-chrome alloy.

6. The wire guide of claim 1 wherein the stop has a spherical shape, and the spherical shape defines a proximal end of the core wire.

7. The wire guide of claim 1 wherein the stop defines a proximal end of the core wire, the stop directly abutting the proximal end of the outer wire to define the predetermined length.

8. A telescopic wire guide configured for insertion through a working channel of an endoscope into a biliary or pancreatic duct, the telescopic wire guide comprising:
   an outer wire having a proximal end and a distal end, the outer wire having a lumen formed from the proximal end through the distal end; and
   a core wire disposed within the lumen and slidably movable therealong relative to the outer wire for distally telescopically extending the wire guide a predetermined length, the core wire comprising a proximal portion and a distal portion, the proximal portion comprising a stop to limit distal movement of the core wire, the distal portion defining a distal end that is retractable into the lumen of the outer wire proximally beyond the distal end of the outer wire, wherein the stop abuts the proximal end of the outer wire to define the predetermined length and defining an extended position in which the core wire extends the predetermined length from the outer wire, the core wire having a first length and the outer wire having a second length, the first length being greater than the second length, the core wire configured to slidably retract from the extended position to a retracted position in which the distal portion is disposed entirely within the lumen and the distal end of the core wire is disposed proximally from the distal end of the outer wire;
   wherein the core wire can be fully withdrawn from the outer wire;
   wherein the telescopic wire guide is configured to allow a medical component to pass over an entire length of the telescopic wire guide while the telescopic wire guide is disposed in a channel port of an endoscope;
   wherein the outer wire is a helical coil defining the lumen formed from the proximal end through the distal end thereof.

9. The wire guide of claim 8 wherein the stop has a spherical shape, and the spherical shape defines a proximal end of the core wire.

10. The wire guide of claim 8 wherein the stop defines a proximal end of the core wire, the stop directly abutting the proximal end of the outer wire to define the predetermined length.

11. A telescopic wire guide configured for insertion through a working channel of an endoscope into a biliary or pancreatic duct, the telescopic wire guide comprising:
   an outer wire having a proximal end and a distal end, the outer wire having a lumen formed from the proximal end through the distal end, the outer wire having a constant outer diameter along its entire length; and
   a core wire disposed within the lumen and slidably movable therealong relative to the outer wire for distally telescopically extending the wire guide a predetermined length, wherein the core wire comprises a proximal portion and a distal portion, the proximal portion comprising a stop to limit distal movement of the core wire, the distal portion defining a distal end that is retractable into the lumen of the outer wire proximally beyond the distal end of the outer wire, wherein the stop abuts the proximal end of the outer wire to define the predetermined length and defining an extended position in which the core wire extends the predetermined length from the outer wire, the core wire configured to slidably retract from the extended position to a retracted position in which the distal portion is disposed entirely within the lumen and the distal end of the core wire is disposed proximally from the distal end of the outer wire;

wherein the outer wire is a helical coil defining the lumen formed from the proximal end through the distal end thereof.

12. The telescopic wire guide of claim 11 wherein the core wire has a first length and the outer wire has a second length, the first length being greater than the second length, wherein the first length is between 400 and 600 centimeters and the second length is between 200 and 300 centimeters.

13. The telescopic wire guide of claim 11 wherein the outer wire comprises super elastic material, stainless steel wire, nitinol, cobalt-chromium-nickel-molybdenum-iron alloy, or cobalt-chrome alloy.

14. The telescopic wire guide of claim 13 wherein the outer wire comprises an outer coat.

15. The telescopic wire guide of claim 14 wherein the outer coat comprises polytetrafluoroethylene.

16. The telescopic wire guide of claim 11 wherein the core wire comprises super elastic material, stainless steel wire, nitinol, cobalt-chromium-nickel-molybdenum-iron alloy, or cobalt-chrome alloy.

17. The telescopic wire guide of claim 11 wherein the stop defines a proximal end of the core wire, the stop directly abutting the proximal end of the outer wire to define the predetermined length.

* * * * *